(12) United States Patent
Bolt (10) Patent No.: US 7,917,307 B2
(45) Date of Patent: Mar. 29, 2011

(54) OIL SAMPLE ANALYSIS CALCULATOR AND METHOD OF USING THE SAME

(75) Inventor: Donald W. Bolt, North Aurora, IL (US)

(73) Assignee: Alstom Transportation Inc., New York, NY (US)

( * ) Notice: Subject to any disclaimer, the term of this patent is extended or adjusted under 35 U.S.C. 154(b) by 0 days.

(21) Appl. No.: 12/188,409

(22) Filed: Aug. 8, 2008

(65) Prior Publication Data

US 2010/0036619 A1 Feb. 11, 2010

(51) Int. Cl.
*G06F 19/00* (2011.01)
*G01N 31/00* (2006.01)

(52) U.S. Cl. ............... 702/22; 73/152.09; 166/250.01; 196/46; 196/155; 208/177; 208/308; 702/100; 702/182

(58) Field of Classification Search .............. 702/22, 702/100, 182; 73/152.09; 166/250.01; 208/177, 208/179, 308; 196/46, 155
See application file for complete search history.

(56) References Cited

U.S. PATENT DOCUMENTS

| | | | |
|---|---|---|---|
| 3,304,255 A * | 2/1967 | Katsuta et al. | 208/179 |
| 3,619,072 A * | 11/1971 | O'Hara et al. | 356/246 |
| 4,746,420 A * | 5/1988 | Darian et al. | 208/222 |
| 5,517,427 A | 5/1996 | Joyce | |
| 5,537,336 A | 7/1996 | Joyce | |
| 6,151,108 A | 11/2000 | Kwon et al. | |
| 6,192,325 B1 | 2/2001 | Piety et al. | |
| 6,776,024 B2 * | 8/2004 | Jakoby | 73/10 |
| 6,859,517 B2 | 2/2005 | Wilson et al. | |
| 6,949,936 B2 | 9/2005 | Stone et al. | |
| 2001/0001851 A1 | 5/2001 | Piety et al. | |
| 2007/0137292 A1 | 6/2007 | Xian et al. | |
| 2009/0145211 A1 * | 6/2009 | Schneider | 73/114.55 |

FOREIGN PATENT DOCUMENTS

EP 0376920 B1 5/1995

OTHER PUBLICATIONS

Marsden, Paul et al., "A Replacement Database for the CH-47D Spectrometric Oil Analysis Program", Airframes and Engines Division, DSTO Aeronautical and Maritime Research Laboratory, 506 Lorimer St, Victoria 3207 Australia, Mar. 2002.

* cited by examiner

*Primary Examiner* — Eliseo Ramos Feliciano
*Assistant Examiner* — Elias Desta
(74) *Attorney, Agent, or Firm* — Cantor Colburn LLP (57) ABSTRACT

In an oil sample analysis calculator (100) for analyzing results of oil samples from an engine, the oil sample analysis calculator (100) includes an input module (110) which receives an input data set (140), a processing module (130) which receives the input data set (140) from the input module (110) and corrects the input data set (140) based on at least one of an amount of oil added to the engine and an amount of oil removed from the engine, and an output module (120) which receives the input data set (140) corrected by the processing module (130) and outputs an output data set (150).

20 Claims, 5 Drawing Sheets

OIL SAMPLE ANALYSIS CALCULATOR AND METHOD OF USING THE SAME

TECHNICAL FIELD

The present disclosure relates generally to an oil sample analysis calculator and, more particularly, to an engine oil sample analysis calculator which corrects for oil changes and additions to accurately predict trends in concentrations of oil contaminants over time.

BACKGROUND

Oil is generally used as a lubricant to reduce friction between moving parts in a mechanical system, such as an engine or a transmission in a locomotive, for example. The oil is free of contaminants when it is first put into the engine, but over time collects wear and corrosion products which contaminate the oil. For example, metal particulates are produced by abrasion or chemical corrosion in the engine during normal operation, and even more so during high duty cycle operations such as those associated with operation of a locomotive engine. Oil filters in the engine remove larger particles from the oil, but smaller contaminants are not removed by the filter, and instead accumulate in the oil over time.

In many industries, and particularly in the railroad transportation industry, it is important to detect impending mechanical failure before the failure occurs or a condition causing the impending failure worsens. To this end, chemical and/or physical analysis of periodic oil samples taken from a locomotive engine can provide an indication of wear status of the locomotive engine and other associated components, such as drive or hydraulic systems. Specifically, analysis of a concentration of the metal particulates in oil over time provides an indication of engine stress or engine wear and, more particularly, analysis of trends in the concentration of metal particulates provides an indication of impending mechanical failure or deteriorating engine conditions. In addition, other types of analyses of the oil, such as testing for the presence of water or other contaminants, as well as trend analysis of concentrations of these other contaminants, provides additional indication of the condition of the engine and any impending mechanical failures thereof. For example, detection of water in the oil may be indicative of a leak in the engine, such as from a deteriorating gasket, for example, while a decreasing flashpoint of the oil may indicate a fuel-to-oil leak.

Typical techniques used to analyze oil include particle size analysis, magnetic chip detection methods, ultrasonic reflectometry, ferrography, x-ray fluorescence and emission spectroscopy, for example. Spectrographic analysis, for example, is a popular method of oil analysis which provides concentrations, typically in parts-per-million (PPM), of metallic substances in the oil. The concentrations are monitored over time, and once a critical concentration (based on a predetermined set point) is reached, maintenance is performed on the engine to prevent any impending failure from occurring.

However, a typical diesel engine used in a locomotive uses a considerable amount of oil during the life cycle of the engine, due to high duty cycle operations associated with railroad transportation. As a result, the oil in a locomotive engine is changed or added to frequently. Changing or adding to the oil in the engine affects concentrations of the contaminants in the oil, and actual trends in these concentrations are thereby lost. This results in a decrease in accuracy of predicting impending engine failures, thereby causing an increase in catastrophic failures and/or resultant corrective maintenance requirements for the engines, also resulting in increased repair costs and down time of the engines.

In addition, manual tracking of trends in concentrations of contaminants in oil is overly cumbersome, particularly for a typical major freight railroad corporation, since these corporations utilize hundreds of locomotives for transportation of freight or passengers. As a result, it is impossible to provide timely feedback of manually-tracked trends in the concentrations of the contaminants in the oil in order to effectively prevent failures in the engines of the locomotives.

Accordingly, it is desired to develop an oil sample analysis calculator which overcomes the problems described above. More specifically, it is desired to develop an oil sample analysis calculator which accurately and efficiently predicts trends in concentrations of oil contaminants when oil is changed and/or added throughout the lifecycle of an engine.

SUMMARY

According to the aspects illustrated herein, there is provided an oil sample analysis calculator for analyzing results of oil samples from an engine. The oil sample analysis calculator includes an input module which receives an input data set, a processing module which receives the input data set from the input module and corrects the input data set based on at least one of an amount of oil added to the engine and an amount of oil removed from the engine, and an output module which receives the input data set corrected by the processing module and outputs an output data set.

According to the other aspects illustrated herein, a method for performing oil sample trend analysis includes: inputting an input data set corresponding to analysis results of an oil sample from an engine to an input module; correcting the input data set based on at least one of an amount of oil added to the engine and an amount of oil removed from the engine to generate a corrected input data set using a processing module connected to the input module; generating a graph of the corrected input data set versus time; and outputting the corrected input data set and the graph of the corrected input data set versus time via an output module.

According to yet other aspects illustrated herein, a method for performing oil sample trend analysis includes inputting an input data set corresponding to analysis results of an oil sample from an engine to an input module. The input data set includes a first oil contaminant concentration corresponding to a first oil sample, a second oil contaminant concentration corresponding to a second oil sample taken after the first oil sample, and a third oil contaminant concentration corresponding to a third oil sample taken after the second oil sample. The method further includes correcting the input data set based on at least one of an amount of oil added to the engine and an amount of oil removed from the engine to generate a corrected input data set using a processing module connected to the input module.

The correcting the input data set includes: comparing the first oil contaminant concentration, the second oil contaminant concentration and the third oil contaminant concentration; removing the second oil contaminant concentration from the input data set when the second oil contaminant concentration is less than the first oil contaminant concentration and the third oil contaminant concentration is greater than the first oil contaminant concentration; and correcting the second oil sample to correspond to a trend based on at least the first oil sample concentration when the second oil contaminant concentration is less than the first oil contaminant concentration and the third oil contaminant concentration is greater than the first oil contaminant concentration but less than the third oil contaminant concentration.

The method further includes generating a graph of the corrected input data set versus time, generating a trend warning and/or rate of change warning based on predetermined set points stored in an output module, and outputting the corrected input data set, the trend warning and/or the rate of change warning, and the graph of the corrected input data set versus time via the output module.

The above described and other features are exemplified by the following figures and detailed description.

BRIEF DESCRIPTION OF THE DRAWINGS

Referring now to the figures, which are exemplary embodiments, and wherein the like elements are numbered alike.

DETAILED DESCRIPTION

Disclosed herein is an oil sample analysis calculator which takes spectrographic data provided from spectrographic analysis of oil, translates the spectrographic data into an oil metal analysis timeline, and converts the oil metal analysis timeline into a corrected historical view of wear metal changes in the oil, including oil sweetening and other changes. In particular, the oil sample analysis calculator according to an exemplary embodiment efficiently and accurately predicts trends in concentrations of oil contaminants when oil is changed and/or added to an engine over the lifecycle of the engine.

Figure 1:
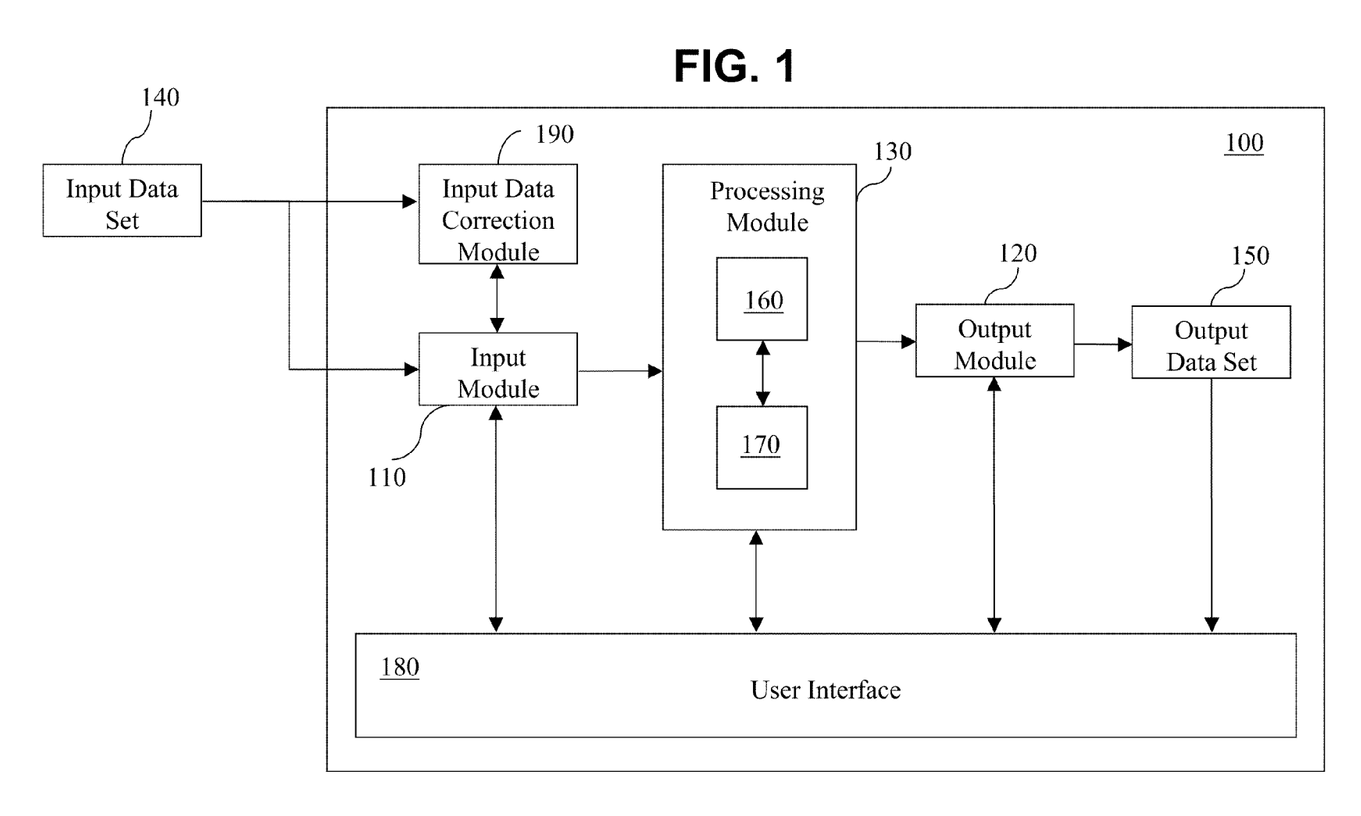
FIG. 1 is a block diagram of an oil sample analysis calculator.

Referring to FIG. 1, of an oil sample analysis calculator 100 according to an exemplary embodiment includes an input module 110, an output module 120 and a processing module 130 connected therebetween. As will be described in further detail below, the input module 110 receives an input data set 140 from outside the oil sample analysis calculator 100 and provides the input data set 140 to the processing module 130. The processing module 130 processes the input data set 140 to produce an output data set 150 based on predetermined parameters and/or set points in the output module 120.

The processing module 130 includes a timeline generation part 160 and a timeline correction part 170, as shown in FIG. 1. The timeline generation part 160 receives input data from the input data set 140 and generates a timeline, e.g., a graph of values of the input data over time. In an exemplary embodiment, the input data set 140 includes levels of contaminants in oil and, more particularly, concentrations of contaminants in oil samples of engine oil taken from a diesel engine in a locomotive used in the railroad industry, as well as geographical and other identifying information related to the locomotive from which a given oil sample is taken.

It will be noted that while exemplary embodiments are described herein with reference to diesel locomotive engines, alternative exemplary embodiments are not limited thereto. For example, the oil sample analysis calculator 100 according to an alternative exemplary embodiment may be used in conjunction with oil samples from different types of engines, such as gasoline engines and, more generally, may be utilized to analyze fluid samples of any type of system or device such as a hydraulic system or other fluid system for which samples therefrom are analyzed over time.

Specifically, the input data set 140 according to an exemplary embodiment includes concentration levels of metallic and/or chemical contaminants in an oil sample, determined by physical and/or spectrographic tests of the oil sample, along with information related to the oil sample itself, such as dates when the oil sample was taken and/or analyzed, a locomotive number which identifies a locomotive from which the oil sample was taken, and a geographic location of the locomotive, for example. More specifically, the input data set 140 may include individual concentration levels (or, alternatively, combined concentration levels) of one or more of iron (Fe), lead (Pb), copper (Cu), tin (Sn), boron (B), nickel (Ni), aluminum (Al), silicon (Si), sodium (Na), chromium (Cr), calcium (Ca), silver (Ag), zinc (Zn) and/or pentane insolubles (PI), as well as water, fuel level and oil additive level. It should be noted that the input data set 140 according to alternative exemplary embodiments is not limited to the abovementioned items. For example, other contaminant levels and/or other properties of the oil (such as viscosity, flashpoint and/or pH, for example) may be included in the input data set 140.

The timeline generation part 160 receives the input data of the input data set 140 and generates a timeline, e.g., a graph, of any or all of the abovementioned items. More particularly, the timeline generation part 160 generates a timeline showing each particular oil sample concentration level and corresponding sample dates thereof. Thus, a general trend for each of the concentration levels can be seen. However, when additional oil is added to a given locomotive engine (or, similarly, when the oil in the locomotive engine is completely changed out) the general trend generated by the generation module 160 using the input data set 140 does not accurately reflect actual trends in concentrations of the contaminants over time. For example, if an oil sample is analyzed immediately after oil has been added to an engine (known as "oil sweetening"), concentrations of contaminants in the sample will be diluted with respect to previous samples taken before the oil was sweetened. Likewise, changing the oil in an engine flushes a significant portion of contaminants out of the engine, and comparing contaminant concentrations in the changed oil with samples taken prior to changing the oil is meaningless. This is particularly troublesome in analyzing oil samples from railroad locomotives, since high duty ratio operations associated therewith require frequent oil adds and/or changes. As a result, actual trends in oil contaminant concentrations are frequently reset, e.g., are lost, and monitored contaminant levels never reach established trip points, even when failure of components in the locomotive engines is imminent. To obviate this problem, the timeline correction part 170 of the oil sample analysis calculator 100 according to an exemplary embodiment accounts for changes in contaminant concentrations in oil samples due to oil sweetening and oil changes. To this end, the timeline correction part 170 includes an algorithm which determines oil adds and/or changes by analyzing the trending of previous oil samples and thereby determines whether to correct a given concentration trend, e.g., historical timeline, based on the same.

Specifically, the algorithm of the timeline correction part 170 according to an exemplary embodiment evaluates concentration trends by monitoring each concentration for which data is included in the input data set 140 over time. Typically, concentrations of contaminants in oil increase over time. Thus, when the algorithm detects a decreased concentration, meaning a concentration for which a given contaminant level has decreased as compared to one or more previous concentrations of the given contaminant, the algorithm looks at a subsequent concentration for the given contaminant, e.g., the next subsequent concentration value. If the next subsequent concentration value returns to an expected concentration, e.g., a concentration greater than the one or more previous concentrations, the algorithm determines that the decreased concentration was an anomalous sample and disregards it.

On the other hand, if the subsequent concentration is also less than the one or more previous concentrations (in the same manner as the decreased concentration) and is greater than the decreased concentration itself, the algorithm determines that an oil add or change has occurred, and corrects all subsequent concentrations of the given contaminant accordingly. More specifically, the algorithm resets the initially-decreased concentration to an interpolated value which corresponds to a predicted value of the concentration at the time of the oil add or change, and thereafter adjusts subsequent concentrations based on the interpolated value. Thus, an actual trend, e.g., a more accurate trend, of contaminant concentrations in oil is maintained, even when oil is added (or completely changed).

As a result, the timeline correction part 170 effectively corrects the input data set 140 to produce a new, corrected data set, e.g., the output data set 150. In addition, the output data set 150, including corrected contaminant concentration trend data, is processed by the output module 120 to compare the output data set 150 with trip points associated with critical contaminant levels to identify potential problems in the engine, as will be described in further detail below.

Still referring to FIG. 1, a user interface 180 is connected to the input module 110, the output module 120 and the processing module 130. In addition, the output data set 150 is provided to the user interface 180. As a result, a user (not shown) is able to view and/or manipulate the input data set 140 using the input module 110, adjust operation of the processing module 130 and the output module 120, and view the output data set 150.

In an exemplary embodiment, the oil sample analysis calculator 100 is implemented using an event-driven database management program embedded in spreadsheet software used for creating charts and graphs from electronic spreadsheets and included in a computer, for example. Specifically, the oil sample analysis calculator 100, and/or any of the abovementioned components thereof, may include a computer, e.g., a microcomputer, implementing MICROSOFT VISUAL BASIC® embedded in a MICROSOFT EXCEL® spreadsheet program in a MICROSOFT WINDOWS® operating system, but alternative exemplary embodiments are not limited thereto.

The oil sample analysis calculator 100 according to an alternative exemplary embodiment further includes an input data correction module 190, as shown in FIG. 1. The input data correction module 190 corrects errors in the input data set 140, such as missing or incorrectly formatted data, for example. Correcting the errors in the input data set 140 may be done either automatically, e.g., without any user input, or, alternatively, manually, e.g., with user input. Specifically, to automatically correct errors, the input data correction module 190 directly receives the input data set 140 from outside the oil sample analysis calculator 100, compares the input data set 140 with a predetermined input data set format, and automatically deletes any individual data points which are erroneous, e.g., do not conform to the predetermined input data set format. Although deleting a single erroneous data point from the input data set 140, or even a number of erroneous data points therefrom, may slightly affect accuracy of the output data set 150, any such affect is minimal and, regardless, allows processing of remaining correct data points of the input data set 140 by the processing module 130, rather than entirely preventing any processing of the input data set 140.

Alternatively, errors in the input data set 140 may be corrected manually by the user. More particularly, the user views the input data set 140 which has been inputted to the input module 110 and, via the user interface 180 and the input data correction module 190, manually corrects any errors in the input data set 140. Since the user can correct many errors in the input data set (such as incorrect data formats, duplicate entries, etc.), rather than deleting an entire data point having an error as in the automatic error correction described above, the accuracy of the output data set 150 is further increased.

Figure 2:
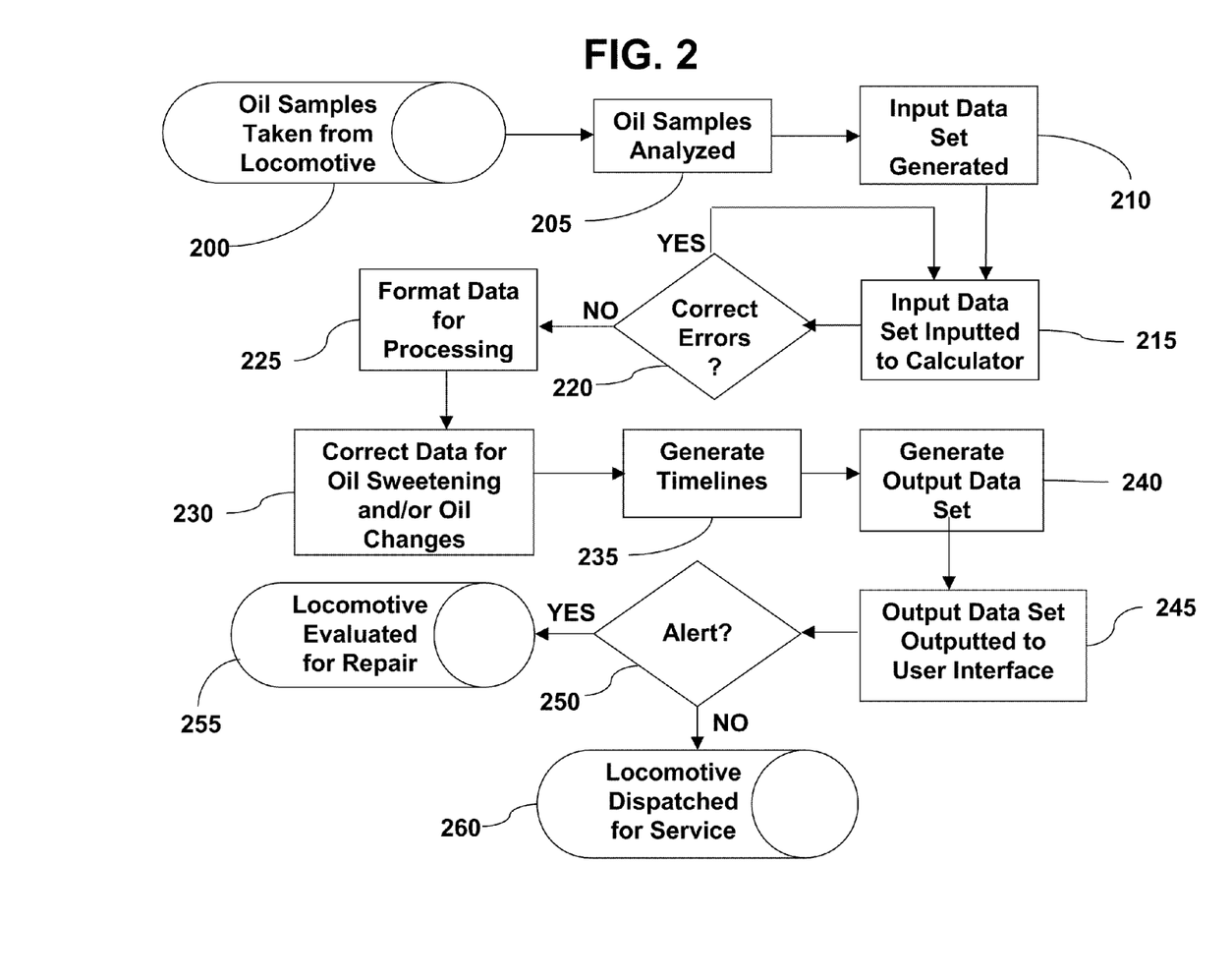
FIG. 2 is a flowchart which illustrates a method of using the oil sample analysis calculator.

A method of using the oil sample analysis calculator 100 according to an exemplary embodiment will now be described in further detail with reference to FIG. 2. In step 200, oil samples are periodically taken from an engine and, more particularly, from a diesel locomotive engine, for example. Then, in step 205, the oil samples are analyzed to determine chemical and/or physical characteristics of the oil sample. The oil samples may be analyzed using mechanical and/or spectrographic analysis methods, but alternative exemplary embodiments are not limited thereto Thereafter, in step 210, results of the analyses in step 205 are compiled into an input data set 140 (see FIG. 1). It will be noted that the oil samples are taken periodically, e.g., over a period of time such as on a weekly or other basis, but that each individual oil sample thereof may be analyzed individually, on a per-sample basis and thereafter compiled into the input data set 140 or, alternatively, the oil samples may be analyzed as a batch, the cumulative results of which are then compiled to produce the input data set 140.

As described above in greater detail with reference to FIG. 1, the input data set 140 according to an exemplary embodiment includes concentration levels of metallic and/or chemical contaminants in the oil sample, as well as information related to each individual oil sample, such as a date when the oil sample was taken and/or analyzed, a locomotive number which identifies the locomotive from which the oil sample was taken, and a geographic location of the locomotive, but alternative exemplary embodiments are not limited thereto.

In step 215, input data set 140 is inputted to the oil sample analysis calculator 100. Specifically, the input data set 140 may be inputted from outside the oil sample analysis calculator 100, as best shown in FIG. 1, or alternatively, the input data set 140 may be inputted to the oil sample analysis calculator 100 by a user, utilizing a batch cut and paste operation between the input data set 140 and the user interface 180, respectively. Thus, an entire input data set 140, including a plurality of data values, e.g., a plurality of individual oil sample analysis results, may be simultaneously inputted to the oil sample analysis calculator 100.

Next, in step 220, errors in the input data set 140 are corrected. As described above in greater detail, the errors may be corrected automatically by the input data correction module 190 (FIG. 1). Alternatively, the errors may be corrected manually, by the user, using the user interface 180, the input module 110 and the input data correction module 190. In yet another alternative exemplary embodiment, the step 220 may be omitted, and in this case the input data set 140 is supplied directly to the processing module 130 (FIG. 1), via the input module 110, without any error correction.

In step 225, the input module 110 formats the input data set 140 for processing by the processing module 130 (FIG. 1). Specifically, the input data set 140 is formatted such that an event-driven database management program may be used to process the input data set 140. Further, the event-driven database management program may be embedded in spreadsheet software in the oil sample analysis calculator 100 and may further be used for creating charts and graphs from the input data set 140, but alternative exemplary embodiments are not limited to the abovementioned components or configurations.

In step 230, the input data set 140 is analyzed using the algorithm described above in greater detail with reference to FIG. 1. Thus, individual data of the input data set 140 are corrected, as required, by the timeline correction part 170 (FIG. 1). Specifically, the individual data are corrected based on whether the algorithm detects oil sweetening or an oil change, as described above in greater detail. Further, anomalous individual data are discarded, while normal data, e.g., data which is neither anomalous nor affected by oil sweetening and/or an oil change, are neither corrected nor discarded, respectively, by the algorithm of the timeline correction part 170.

In step 235, oil sample analysis timelines are generated. Specifically, the corrected data are used by the timeline generation part 160 (FIG. 1) to generate an oil sample timeline which is corrected for oil sweetening and changes, as will be described below with reference to FIG. 3. At the same time, uncorrected data are used to generate a comparative oil sample timeline for purposes of comparison (see FIG. 4).

In addition to generating the oil sample timelines, the oil sample analysis calculator according to an exemplary embodiment uses the corrected oil sample analysis data to generate an output data set 150 (step 240), based on predetermined parameters, criteria and/or set points in the output module 120 (FIG. 1). Specifically, the output data set 150 according to an exemplary embodiment includes the corrected oil sample analysis data, as described above, as well as additional parameters, based on the corrected oil sample analysis data, and with which the operator makes determinations regarding servicing the locomotive from which the oil samples came.

More specifically, in step 245, the output data set 150 is outputted to the user interface 180 (FIG. 1), wherein the operator views the input data set 140, the corrected oil sample analysis data, corrected and comparative oil sample timelines, as well as any alerts generated based on the predetermined set points. Based on whether an alert is generated (step 250), the user may either further evaluate the associated locomotive for repair (step 255) or dispatch the locomotive for service (step 260).

Figure 3:
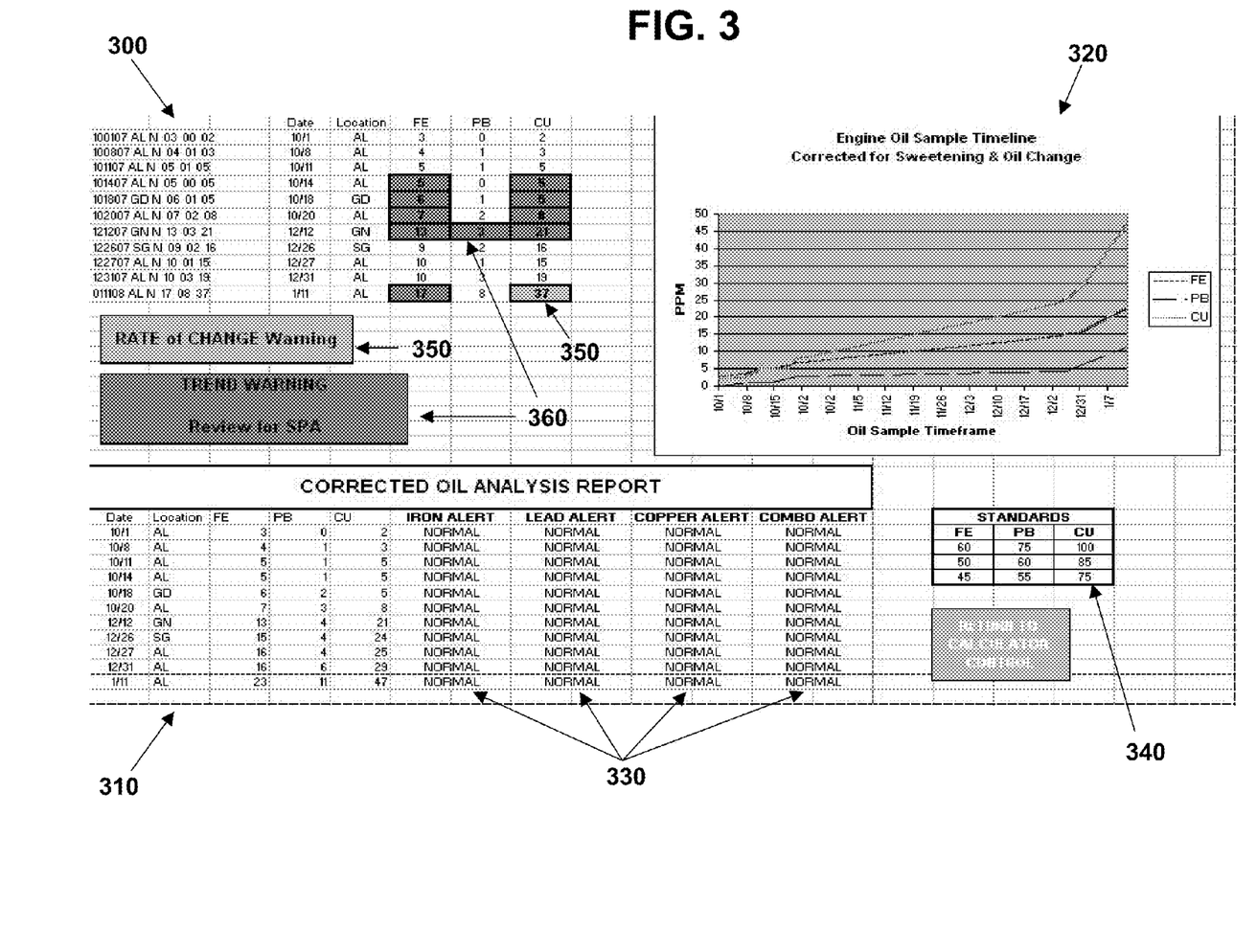
FIG. 3 is a screenshot of an output screen of the oil sample analysis calculator.

An output screen of the oil sample analysis calculator 100 according to an exemplary embodiment will no be described in further detail with reference to FIG. 3. For purposes of simplicity in illustration, note that only three contaminants, i.e., iron (Fe), lead (Pb) and copper (Cu) are shown in FIG. 3, but exemplary embodiments are not limited thereto. As shown in FIG. 3, an output screen includes, but is not limited to, an input data section 300, a corrected data section 310, an engine oil sample timeline 320, an alerts section 330, and an alert settings section 340.

The input data section 300 includes at least a portion of the input data set 140 (FIG. 1) in a spreadsheet format. This allows the user to view pre-corrected data, e.g., input data, at the same time as corrected data. To this end, the corrected data section 310 includes a corrected oil sample analysis report, also in a spreadsheet format, corrected for oil sweetening and/or oil changes, as described in greater detail above.

The engine oil sample timeline 320 includes a graph of contaminant concentrations, in parts-per-million (PPM), which graphically illustrates the data in the corrected oil sample analysis of the corrected data section 310. In an alternative exemplary embodiment, the graph shown in FIG. 3 may be replaced by, or supplemented with, a comparative oil sample analysis graph, as will be described below with reference to FIG. 4.

The corrected data section 310 includes the alerts section 330, which provides alerts, e.g., alarms based on predetermined set points, as shown in the alert settings section 340. In addition to text alerts provided in the corrected data section 310 (note that there are no alerts in FIG. 3; all data points are normal), graphical alerts, such as a rate of change warning 350 and/or a trend warning 360, are provided, as appropriate, in the output screen of the oil sample analysis calculator 100 according to an exemplary embodiment. It will be noted that, as illustrated in FIG. 3, both a rate of change warning 350 and a trend warning 360 were generated based on the uncorrected input data shown in the input data section 300, but were both eliminated after correction of the input data, shown in the corrected data section 310. Thus, in addition to providing the corrected oil analysis report including an accurate timeline of trends in concentrations of oil contaminants, even when oil is changed and/or added, the oil sample analysis calculator 100 according to an exemplary embodiment further reduces false alarms which are generated based incorrect alerts triggered by uncorrected oil sample data.

Figure 4:
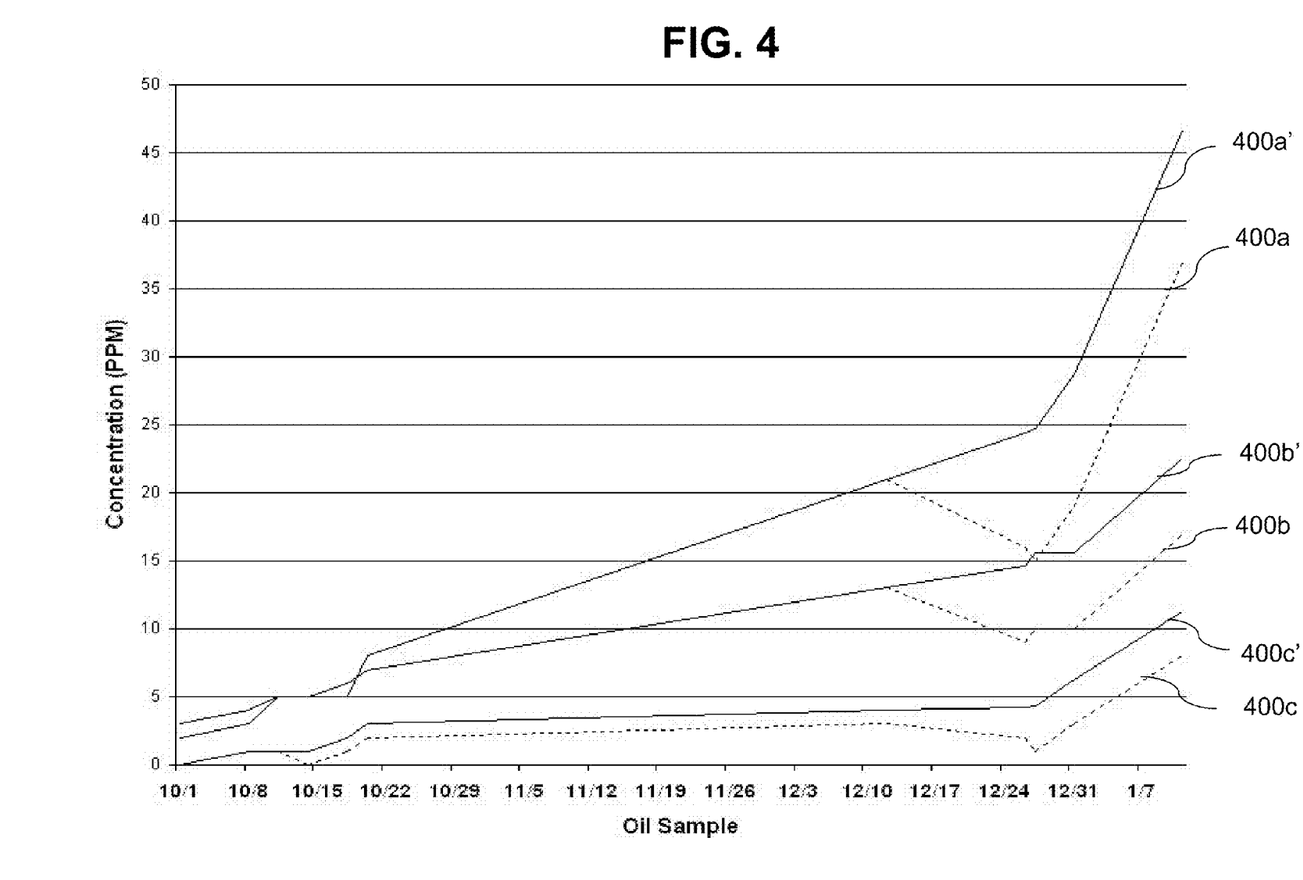
FIG. 4 is a screenshot of a comparative output of the oil sample analysis calculator illustrating uncorrected and corrected oil sample analysis timelines.

Referring now to FIG. 4, a comparative output of the oil sample analysis calculator illustrates uncorrected and corrected oil sample analysis timeliness Therefore the operator can visually compare uncorrected oil sample analysis data with corrected oil sample analysis data. Specifically, FIG. 4 illustrates concentration comparisons over time between: an uncorrected copper trend 400*a* and a corrected copper trend 400*a'*; an uncorrected iron trend 400*b* and a corrected iron trend 400*b'*; and an uncorrected lead trend 400*c* and a corrected lead trend 400*c'*. Thus, as shown in FIG. 4, it can be determined, for example, that an oil add or change occurred for a sample between approximately the dates of 12/24 and 1/7 (on the x-axis of FIG. 4) at which point the corresponding trends were corrected to account for the oil add or change. As a result, the data for each of the copper, iron and lead analyses thereof has been corrected and is thereby more accurately shown in the corrected trends of FIG. 4.

Figure 5:
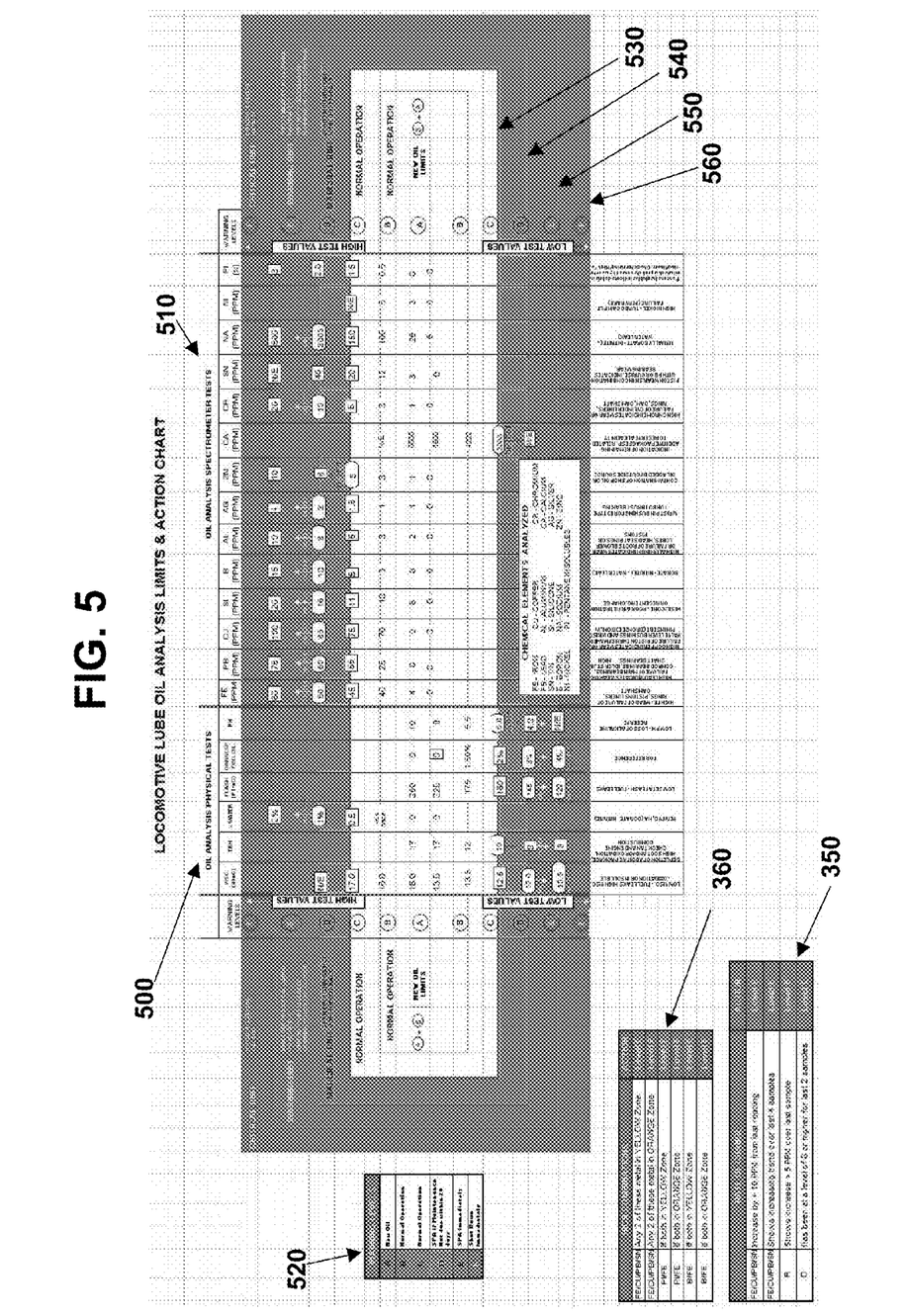
FIG. 5 is a screenshot of an output of the oil sample analysis calculator illustrating an oil sample analysis decision sheet.

A screenshot of an output of the oil sample analysis calculator 100 illustrating an oil sample analysis decision sheet according to an exemplary embodiment will now be described in further detail with reference to FIG. 5. To further aid the user in evaluating whether corrective action is required (steps 245 and 250 of FIG. 2) based upon the output data set 140 (FIG. 1), an oil sample analysis decision sheet is provided, as shown in FIG. 5. The oil sample analysis decision sheet includes summary results of physical analyses 500 and summary results of spectrometer analyses 510 performed on an oil sample. Individual warning levels 550 are provided for each analysis. Specifically, in an exemplary embodiment, a result of each analyses is grouped, based on the set points of the output module 120 (FIG. 1), into one of several status groups of a plurality of status groups 520, including "New Oil", "Normal Operation", "Maintenance Required", or "Shutdown Immediately", for example, but not being limited thereto. Furthermore, the rate of change warning 350 and the trend warning 360 (FIG. 3) are displayed in the oil sample analysis decision sheet. In addition, to further aid the user in identifying whether alerts require action, the summary results of the physical analyses 500 and the summary results of the spectrometer analyses 510 are graphically grouped into four (4) regions, each region corresponding to an operating condition of a given locomotive. Specifically, the regions include a normal unit operating region 530, a marginal unit operating region 540, a warning unit operating region 550 and a critical unit operating region 560, as shown in FIG. 5. Therefore, the user of the oil sample analysis calculator 100 according to an exemplary embodiment can identify, at a glance, an operational status of a locomotive with respect to a given physical or spectrometric analysis result without needing to study or evaluate individual data values and/or trends in data associated with the abovementioned analyses.

Thus, as described herein, an oil sample analysis calculator according to an exemplary embodiment accurately predicts trends in concentrations of oil contaminants, even when oil is changed and/or added during the lifecycle of an engine. As a result, the oil sample analysis calculator provides a basis for accurate determination of impending engine failure, allowing a user to take appropriate action to substantially mitigate or effectively prevent the impending failure.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof Therefore, it is intended that the invention not be limited to the particular embodiment disclosed as the best mode contemplated for carrying out this invention, but that the invention will include all embodiments falling within the scope of the appended claims.

What is claimed is:

1. An oil sample analysis calculator for analyzing results of oil samples from an engine, the oil sample analysis calculator comprising:
   an input module which receives an input data set, the input data set includes concentration levels of at least one of metallic and chemical contaminants in an oil sample;
   a processing module which receives the input data set from the input module and corrects the input data set based on at least one of an amount of oil added to the engine and an amount of oil removed from the engine; and
   an output module which receives the input data set corrected by the processing module and outputs an output data set,
   wherein the output data set comprises one of a trend warning and a rate of change warning based on a predetermined set point,
   wherein the input data set comprises:
      a first oil contaminant concentration corresponding to a first oil sample;
      a second oil contaminant concentration corresponding to a second oil sample taken after the first oil sample; and
      a third oil contaminant concentration corresponding to a third oil sample taken after the second oil sample, and
   wherein the processing module comprises an algorithm which compares the first oil contaminant concentration, the second oil contaminant concentration and the third oil contaminant concentration for generating the output data set.

2. The oil sample analysis calculator of claim 1, wherein the engine is a diesel engine.

3. The oil sample analysis calculator of claim 2, wherein the engine is a railroad locomotive engine.

4. The oil sample analysis calculator of claim 1, further comprising an input data correction module connected to the input module, wherein the input data correction module additionally corrects errors in the input data set before the input data set is received by the processing module.

5. The oil sample analysis calculator of claim 1, wherein the input data set comprises at least one of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH.

6. The oil sample analysis calculator of claim 5, wherein the output data set comprises at least one of one of corrected iron (Fe) concentration, corrected lead (Pb) concentration, corrected copper (Cu) concentration, corrected tin (Sn) concentration, corrected boron (B) concentration, corrected nickel (Ni) concentration, corrected aluminum (Al) concentration, corrected silicon (Si) concentration, corrected sodium (Na) concentration, corrected chromium (Cr) concentration, corrected calcium (Ca) concentration, corrected silver (Ag) concentration, corrected zinc (Zn) concentration, corrected pentane insolubles concentration, corrected fuel concentration, corrected oil additive concentration, corrected viscosity, corrected flashpoint and corrected pH.

7. The oil sample analysis calculator of claim 6, wherein the processing module comprises:
   a timeline generation part which generates a graph of the at least one of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH versus time; and
   a timeline correction part connected to the timeline generation part, wherein the timeline correction part corrects the at least one of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH, based on the at least one of the amount of oil added to the engine and the amount of oil removed from the engine, to generate a graph of the at least one of one of corrected iron (Fe) concentration, corrected lead (Pb) concentration, corrected copper (Cu) concentration, corrected tin (Sn) concentration, corrected boron (B) concentration, corrected nickel (Ni) concentration, corrected aluminum (Al) concentration, corrected silicon (Si) concentration, corrected sodium (Na) concentration, corrected chromium (Cr) concentration, corrected calcium (Ca) concentration, corrected silver (Ag) concentration, corrected zinc (Zn) concentration, corrected pentane insolubles concentration, corrected fuel concentration, corrected oil additive concentration, corrected viscosity, corrected flashpoint and corrected pH versus time.

8. The oil sample analysis calculator of claim 1, wherein the input data set comprises two or more of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na)

concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH, and the at least two or more of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH are inputted to the input module simultaneously.

9. The oil sample analysis calculator of claim 1, wherein the predetermined set point is included in the output module.

10. The oil sample analysis calculator of claim 1, wherein
the algorithm removes the second oil contaminant concentration from the input data set when the second oil contaminant concentration is less than the first oil contaminant concentration and the third oil contaminant concentration is greater than the first oil contaminant concentration, and the algorithm corrects the second oil sample to correspond to a trend based on at least the first oil sample concentration when the second oil contaminant concentration is less than the first oil contaminant concentration and the third oil contaminant concentration is greater than the first oil contaminant concentration but less than the second oil contaminant concentration.

11. The oil sample analysis calculator of claim 10, wherein the first oil contaminant concentration, the second oil contaminant concentration and the third oil contaminant concentration comprise one of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH.

12. A method for performing oil sample trend analysis, the method comprising:
inputting an input data set corresponding to concentration levels of at least one of metallic and chemical contaminants of an oil sample from an engine to an input module;

correcting the input data set based on at least one of an amount of oil added to the engine and an amount of oil removed from the engine to generate a corrected input data set using a processing module connected to the input module;

generating a graph of the corrected input data set versus time; and outputting the corrected input data set and the graph of the corrected input data set versus time via an output module, wherein the corrected input data set comprises one of a trend warning and a rate of change warning based on a predetermined set point, wherein the input data set comprises:
a first oil contaminant concentration corresponding to a first oil sample;
a second oil contaminant concentration corresponding to a second oil sample taken after the first oil sample; and
a third oil contaminant concentration corresponding to a third oil sample taken after the second oil sample, and wherein the correcting the input data set based on the at least one of the amount of oil added to the engine and the amount of oil removed from the engine comprises:
comparing the first oil contaminant concentration, the second oil contaminant concentration and the third oil contaminant concentration for outputting the corrected input data set and the graph of the corrected input data set versus time.

13. The method of claim 12, further comprising additionally correcting errors in the input data set using an input data correction module before the correcting the input data set based on the amount of oil added to the engine and the amount of oil removed from the engine.

14. The method of claim 12, wherein
removing the second oil contaminant concentration from the input data set when the second oil contaminant concentration is less than the first oil contaminant concentration and the third oil contaminant concentration is greater than the first oil contaminant concentration; and correcting the second oil sample to correspond to a trend based on at least the first oil sample concentration when the second oil contaminant concentration is less than the first oil contaminant concentration and the third oil contaminant concentration is greater than the first oil contaminant concentration but less than the third oil contaminant concentration.

15. The method of claim 14 wherein the first oil contaminant concentration, the second oil contaminant concentration and the third oil contaminant concentration comprise one of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH.

16. The method of claim 12, wherein
the outputting the corrected input data set and the graph of the corrected input data set versus time comprises outputting the one of a trend warning and a rate of change warning, and the predetermined set point is stored in the output module.

17. The method of claim 12, wherein the engine is a diesel locomotive engine.

18. A method for performing oil sample trend analysis, the method comprising:
inputting an input data set corresponding to analysis results of an oil sample from an engine to an input module, the input data set comprising:
a first oil contaminant concentration corresponding to a first oil sample;
a second oil contaminant concentration corresponding to a second oil sample taken after the first oil sample; and
a third oil contaminant concentration corresponding to a third oil sample taken after the second oil sample;

correcting the input data set based on at least one of an amount of oil added to the engine and an amount of oil removed from the engine to generate a corrected input data set using a processing module connected to the input module, the correcting the input data set comprising:
comparing the first oil contaminant concentration, the second oil contaminant concentration and the third oil contaminant concentration;

removing the second oil contaminant concentration from the input data set when the second oil contaminant concentration is less than the first oil contaminant concentration and the third oil contaminant concentration is greater than the first oil contaminant concentration; and correcting the second oil sample to correspond to a trend based on at least the first oil sample concentration when the second oil contaminant concentration is less than the first oil contaminant concentration and the third oil contaminant concentration is greater than the first oil contaminant concentration but less than the second oil contaminant concentration;

generating a graph of the corrected input data set versus time;

generating one of a trend warning and rate of change warning based on a predetermined set point stored in an output module; and outputting the corrected input data set, the one of a trend warning and rate of change warning and the graph of the corrected input data set versus time via the output module.

19. The method of claim 18, further comprising additionally correcting errors in the input data set using an input data correction module before the correcting the input data set based on the at least one of an amount of oil added to the engine and the amount of oil removed from the engine.

20. The method of claim 18, wherein the first oil contaminant concentration, the second oil contaminant concentration and the third oil contaminant concentration comprise one of iron (Fe) concentration, lead (Pb) concentration, copper (Cu) concentration, tin (Sn) concentration, boron (B) concentration, nickel (Ni) concentration, aluminum (Al) concentration, silicon (Si) concentration, sodium (Na) concentration, chromium (Cr) concentration, calcium (Ca) concentration, silver (Ag) concentration, zinc (Zn) concentration, pentane insolubles concentration, fuel concentration, oil additive concentration, viscosity, flashpoint and pH, and the first oil contaminant concentration, the second oil contaminant concentration and the third oil contaminant concentration are simultaneously inputted to the input module.

* * * * *

UNITED STATES PATENT AND TRADEMARK OFFICE
CERTIFICATE OF CORRECTION

| | | |
|---|---|---|
| PATENT NO. | : 7,917,307 B2 | Page 1 of 1 |
| APPLICATION NO. | : 12/188409 | |
| DATED | : March 29, 2011 | |
| INVENTOR(S) | : Donald W. Bolt | |

It is certified that error appears in the above-identified patent and that said Letters Patent is hereby corrected as shown below:

In column 6, line 24, Delete "thereto" and insert -- thereto. --, therefor.

In column 7, line 48, Delete "no" and insert -- not --, therefor.

In column 8, line 27, Delete "timeliness" and insert -- timelines. --, therefor.

In column 10, line 12, In claim 6, Delete "one of one of" and insert -- one of --, therefor.

In column 10, line 49, In claim 7, Delete "one of one of" and insert -- one of --, therefor.

Signed and Sealed this
Twenty-second Day of January, 2013

David J. Kappos
*Director of the United States Patent and Trademark Office*